US006776778B2

(12) United States Patent
Prince

(10) Patent No.: US 6,776,778 B2
(45) **Date of Patent: *Aug. 17, 2004**

(54) NASAL DOUCHE

(76) Inventor: Allen L. Prince, 1502 Oak Glen Trail, Dallas, TX (US) 75232

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/740,305

(22) Filed: Dec. 18, 2000

(65) Prior Publication Data

US 2002/0077621 A1 Jun. 20, 2002

(51) Int. Cl.[7] .................... A61M 31/00; A61M 11/00; A61J 7/00

(52) U.S. Cl. .................... 604/514; 604/78; 604/94.01

(58) Field of Search .................... 604/77–79, 500, 604/512, 513, 514, 516, 94.01; 220/203.19, 203.2, DIG. 13, DIG. 14; 215/DIG. 3; D7/509, 510, 302; D24/224, 117; 229/400–405, 906.1

(56) References Cited

U.S. PATENT DOCUMENTS 1,543,209 A * 6/1925 Fulton .................... 604/78
2,292,568 A * 8/1942 Kanter .................... 128/203.28
3,847,145 A * 11/1974 Grossan .................... 601/160
3,917,119 A * 11/1975 Kahn .................... 222/108
5,116,311 A * 5/1992 Lofstedt .................... 128/200.22
5,175,152 A * 12/1992 Singh .................... 514/162
5,417,652 A * 5/1995 Scott, Sr. .................... 604/19
6,520,384 B2 * 2/2003 Mehta .................... 222/211
6,540,718 B1 * 4/2003 Wennek .................... 604/94.01
6,561,188 B1 * 5/2003 Ellis .................... 128/206.11

* cited by examiner

*Primary Examiner*—Michael J. Hayes
(74) *Attorney, Agent, or Firm*—Allen L. Prince

(57) ABSTRACT

A method and device for filling or partially filling the nasal cavities of a person through both nostril openings with a liquid essentially while the head of the person is at a safe forward angle of tilt by pooling or tubing means for establishing communication of liquid with the nasal cavity of the person and by inhalation or external pressure allowing any liquid exiting the rear of the nasal cavities to drain into the back of the oral cavity of the mouth and embodiments of the device requiring the head of the user to be at a prescribed or greater angle of tilt during use by comprising spilling or shutting off means for assuring the head of the person is at least at a prescribed forward angle of tilt during use.

3 Claims, 2 Drawing Sheets

NASAL DOUCHE

FIELD OF THE INVENTION

This invention relates to a method and device for introducing a stream of liquid into the nasal cavities of the head. This is a continuation of application Ser. No. 09/740,305.

BACKGROUND OF THE INVENTION

The application of liquids to the membranes lining the nasal cavities of the head of a person as a means of treatment is well known. One method is to spray liquid into the nostrils where the liquid is of thin consistency and another is to administer drops into the nostrils where the liquid may have a thicker consistency or is an oil.

Another device, the subject of the SCOTT patent, U.S. Pat. No. 5,417,652, May 23, 1995, is a cup containing a liquid that facilitates inhaling the liquid while the nose is inserted in a specially shaped opening in the side wall of the cup while the patient's head and the cup is maintained in generally upright position. The drawback with the method is that the method or the device obviously does not allow introduction of liquid into the nasal cavity while the head is tilted forward greater than generally upright.

Other devices allow introducing liquid through one nostril under pressure while the head is tilted, the liquid reaching the posterior end of the septum to naturally drain out the other open nostril precluding the possibility of introducing the liquid by inhalation or filling the nasal cavity beyond the posterior end of the septum, or if the other nostril is closed, only a portion of the nasal cavity is filled, excluding the region along the septum on the side of the closed nostril and thus fail to enable completely filling the nasal cavity to the maximum extent possible.

Prior art descriptions of methods and devices for infusing the nasal cavity with liquid have simply mistakenly viewed allowance of liquid to enter the pharynx from the rear of the nasal cavity as a risk and undesirable, LOFSTEDT, U.S. Pat. No. 5,116,311, even though anatomically a person is fully able to voluntarily close the pharynx below the rear opening of the oral cavity to prevent liquid entering the lungs diverting the liquid into the mouth when liquid is received into the pharynx through the nasal cavity under external pressure.

When liquid is being inhaled through the nasal cavity into the pharynx and when anatomically the person's head is in the face forward tilted position, it has not been described in the prior art that any liquid leaving the rear of the nasal cavity into the pharynx over the soft palate will pass directly into the oral cavity, if allowed to be open, by force of gravity as it passes down a diagonally or horizontally oriented pharynx. If the precaution is taken of assuring the head and thus the pharynx of the person is held at an angle of forward tilt in gravity and not a generally upright position, the rear opening of the oral cavity naturally along the floor of the pharynx in gravity, functions as a sink into which the liquid may drain to be expelled out the mouth. While the benefits of washing some regions of the nasal cavity while the head is tilted has been described in the prior art, tilting the head forward has not been described as a risk reduction measure while allowing liquid into the pharynx.

SUMMARY OF THE INVENTION

It is an object of this invention to provide a method and device for filling beyond the end of the septum or partially filling the forward regions along both sides of the septum of the nasal cavity of the head of a person with a liquid by inhalation or external pressure through the nostril openings while the head is safely tilted forward allowing controlled submersion and washing of the nasal cavity simultaneously in both regions along side the septum and the region behind the septum into the pharynx and embodiments comprising means for assuring that the head is at a safe angle of forward tilt during use while the liquid is being infused into the nasal cavity.

DETAILED DESCRIPTION OF THE DRAWINGS

Figure 2:
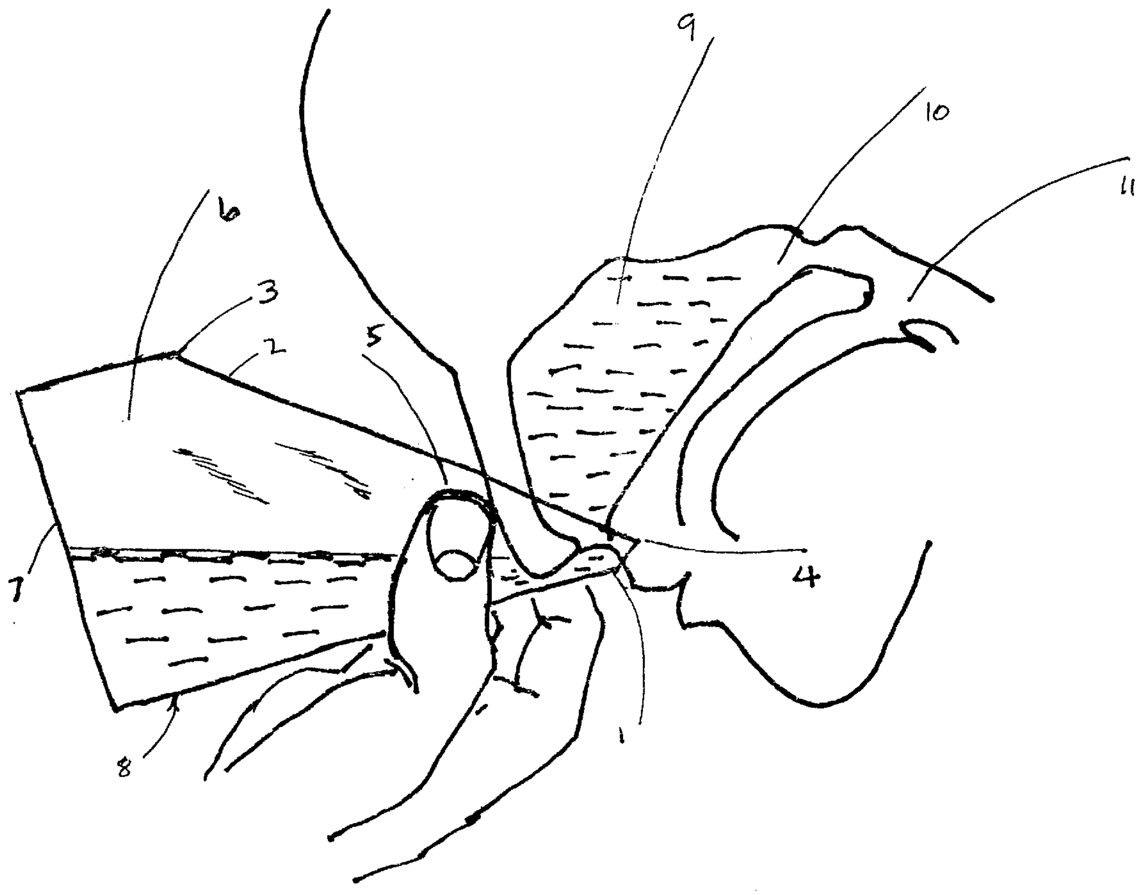
FIG. 2 is a drawing containing a see-through view of the embodiment shown in FIG. 1 containing liquid and a cutaway view of the head of a person properly using the embodiment according to the method of the invention.
Figure 4:
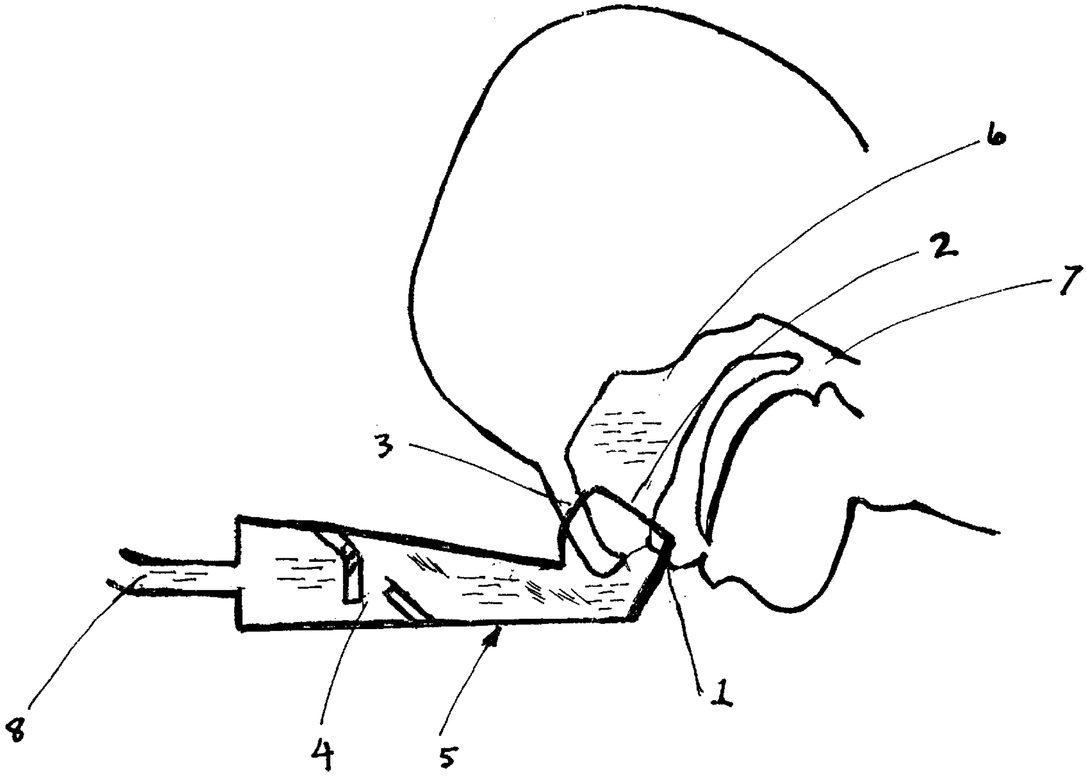
FIG. 4 is a drawing containing a see-through view of the embodiment shown in FIG. 3 and a communicating container capable of imparting external pressure and communicated liquid through both nostril openings and a cutaway view of the head of a person using it while the head is safely tilted forward according to the method of the invention.

FIGS. 2 and 4 illustrate that when the head is tilted forward the cavities function as a container with the rear opening at the top allowing liquid to wash the membranes of the sides and top of the cavities. Approximately the front half of the cavities, above the hard palate, is divided by the septum to form the two nasal cavities. The drawing illustrates that liquid introduced into one nostril opening will fill one of the nasal cavities to the end of the septum (9,17) and spill over into the other nasal cavity without reaching the cavity above the soft palate (10). Introducing liquid into both nostrils fills both nasal cavities and the cavity above the soft palate (10) and any excess liquid leaving the rear over the soft palate naturally flows to (11) and safely falls into the rear of the oral cavity (18) and into the mouth but only while the head is safely tilted forward. The term "nasal cavity" properly refers to one of the cavities on either side of the septum above the hard palate, the cavity behind and above the soft palate (10) to just behind the rear opening into the oral cavity is properly referred to as the nasal pharynx (11) and the cavity at the rear opening into the mouth is properly referred to as oral pharynx (18). The terms "nasal cavities" and "nasal cavity" as used herein refer to all the cavities above the hard and the soft palate and the oral pharynx to the extent it is physically possible to be involved.

Figure One

Figure 1:
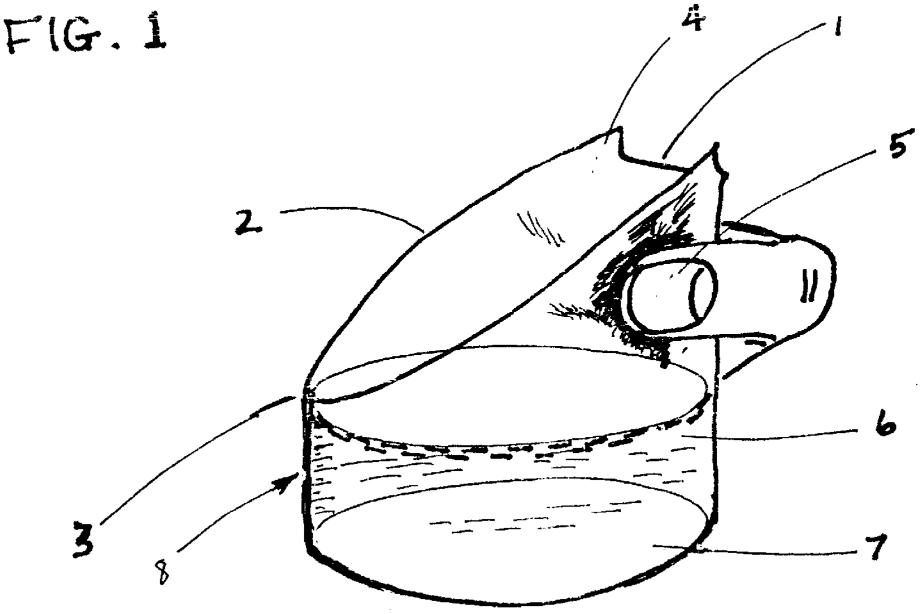
FIG. 1 is a drawing containing a see-through view of an embodiment of the invention containing liquid.

FIG. 1 is a see through drawing that shows a single reservoir open embodiment having a single opening at one end of a flexible cylindrical wall, the opening having a rim that is lower in front (3) and trimmed in the back to fit against a person's face forming a contact region (1) along the rim for contact with the face of a person and a circular bottom (7) closing the cylinder opposite the opening to form a cup as the reservoir. The cup is shown filled near its maximum depth while held upright (3) and the wall is shown being shaped by a person's thumb (5) and fingers increasing the curvature of the wall along the contact region of the cup.

Figure two

FIG. 2 is a see through drawing of the cup shown in FIG. 1 illustrating its proper use showing the container is open over the nose during use exposing the interior to the atmosphere.

Means for establishing communication between the liquid and the nasal cavities is the region of the back wall below the contact region which transports the liquid from the reservoir to the contact region of the cup and the face to form a pool and an air tight communication between the liquid and the nasal cavities which is the nostrils submerged in the pool and the contact region of the cup is in contact with the face below and along each side of the nose, herein referred to as cheek seal contact.

Means for filling or partially filling the nasal cavity is inherently the back side of the cup when the rim along the contact region is in contact with the face allowing the formation of the pool of the liquid submerging the nostril openings to allow the person to inhale the liquid through the nostril openings while the cup is at its angle of fit where the angle of fit of the embodiment is an acute angle the cup forms with the face while maintaining cheek seal contact which varies with the amount of liquid in the pool requiring the angle to be more acute by raising the bottom of cup closer to the forehead as the amount of liquid is reduced.

Means for assuring the head is at a safe angle of forward tilt is inherent in the tapered wall of the cup approaching the contact region (1) allowing the pool to form only while the cup is at an acute angle with the face as shown, contacting the face below (1) and along each side of the nose as cheek seals (4) with the assistance of the curvature of the container wall which may be adjusted by pressing the sides of the container with the thumb (5) and fingers but when the cup is held at greater angles such as when perpendicular to the face, either the nose fails to dip into the liquid if a pool is formed preventing the liquid from submerging the nostrils or the liquid is removed from communication with the nasal cavities either by the contact region failing to contact the face along the sides of the nose, only contacting the face just under the nose, subsequently preventing the liquid from submerging the nostrils by allowing substantially all of the liquid in the reservoir to spill out the open regions of the contact region of the cup that would form the cheek seals, herein referred to as the cheek seals, or if the head is held upright while the container is at the acute angle allowing the cheek seals to contact the face and the nose to dip into the liquid, subsequently preventing the liquid from submerging the nostrils by allowing substantially all of liquid in the reservoir to spill out the opening above the pool over the rim and the cheek seals.

Figure Three

Figure 3:
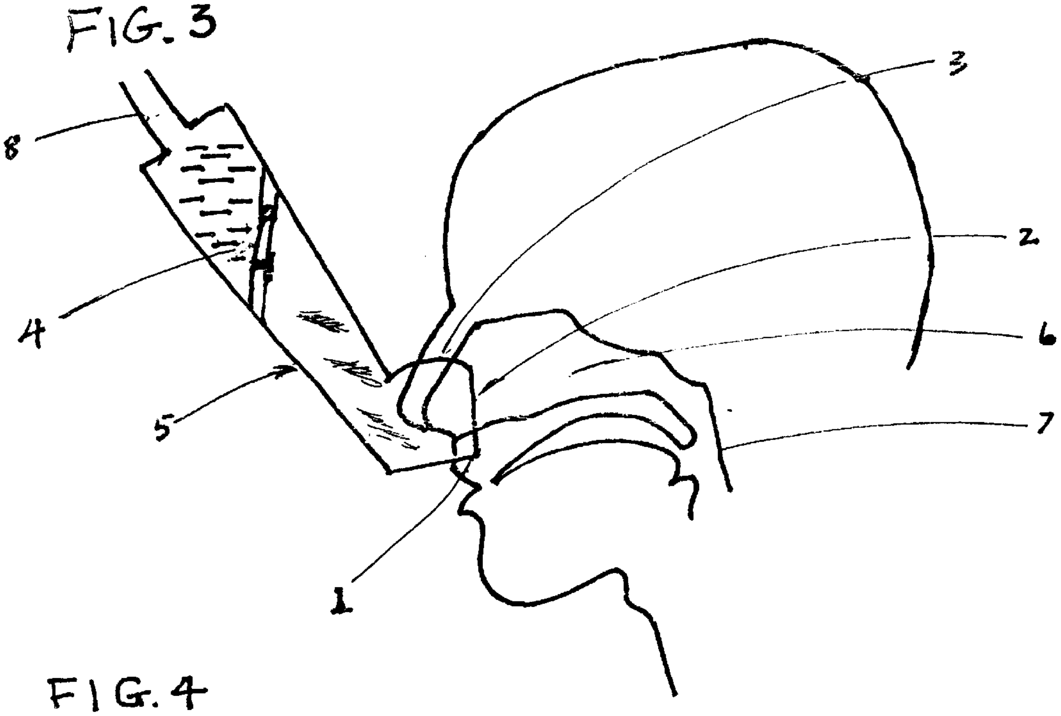
FIG. 3 is a drawing containing a see-through-view of an embodiment of the invention containing liquid and a cutaway view of the head of a person using it in a generally upright position contrary to the method of the invention and the safety mechanism of the invention preventing communication of the liquid through the nostril openings.

FIG. 3 is a see through drawing that shows an irregularly shaped container (16) as a closed embodiment having two openings to the exterior, one opening is a vent between the interior of the container and the exterior (19) and the other opening having a rim trimmed so that the entirety of which is the contact region that contacts the face when the container is placed against the face at its angle of fit as shown, the contact region in full contact with the face of a person forms a pressure tight seal below (12), along each side (13) and over (14) the nose fixing the angle of the device with the face at its angle of fit. Means for establishing communication and for filling the nasal cavity is present as shown in FIG. 4 but is temporarily disabled by means for assuring the head is safely tilted forward because the device is in contact with the face at its angle of fit and the head of the person is generally upright.

Means for assuring the head is safely tilted forward is a partition dividing the interior of the container into two non-communicating distal and proximal reservoirs separated by the partition (15) that is sloped with respect to the container and approximately parallel with the face while the container is at its angle of fit, the partition having a passageway for communicating liquid between the reservoirs that is closed by a hinged flap retaining the liquid in the distal reservoir from entering the proximal reservoir as shown and from entering the nostril openings of the person's nose while the head of the person is held generally upright.

Figure Four

FIG. 4 is a see through drawing that shows the closed embodiment (16) of FIG. 3 in contact with the face at its angle of fit as in FIG. 3.

Means for establishing communication between the liquid in the container and the nasal cavity through the nostril openings is the container with the opening in contact with the face maximally at all points along the rim of the opening, or minimally below (12) and along the sides of the nose (13), with the nostrils submerged in the pool formed at the contact region of the opening and the head of the person safely tilted forward allowing the hinged flap in the partition (15) to hang vertically open in the liquid allowing the liquid in the distal reservoir to communicate with the nasal cavities through the proximal reservoir and through the nostril openings, and through the vent connected to a syringe (21) communicating the interior of the container with the interior of the syringe (20).

Means for filling or partially filling the nasal cavities through the nostrils is the syringe and the plunger continuously feeding liquid through the communicating nostril openings and the container at least in contact with the face below and along the sides of the nose and open over the nose if using inhalation and closed over the nose if using pressure forming a pressure tight seal for increasing the pressure external to the nasal cavity within the container by depressing the plunger of the syringe forcing. the liquid through the nostril openings and into the nasal cavities and beyond.

DETAILED DESCRIPTION OF THE INVENTION

All embodiments of the device shown in the drawings fit over the nose of a person being either open in FIG. 2 or closed in FIG. 4 embodiments having an angle of fit that allows a means of communication of a liquid through the nostril openings by an airtight connection between an external source of the liquid and the nasal cavity. The angle of fit is the angle that the device fits against the face below the nose (1,12) and other points of contact with the face comprising points on the cheeks along the sides the nose of the person (4,13) and over the nose in closed embodiments (14). FIGS. 1 and 2 are open embodiments of the device of the invention and FIGS. 3 and 4 are closed embodiments, meaning closed over the nose embodiments. Both embodiments shown in the drawings show a pooling means of communication of the liquid into the nasal cavity wherein the points of contact along the cheeks essentially form a liquid tight seal against the face of the person below (1,12) and along side the nose (4,13) when the device is placed against the face to allow formation of a pool of the liquid into which the nostrils of the person may be submerged.

FIG. 3 shows the head of the person in a generally upright position and the device in contact with the face at its angle of fit. A shut off means is a flap (15) as a valve preventing flow from the reservoir into the pool limiting the amount of liquid entering the nasal cavity. If liquid were allowed into the nasal cavity while the head of the person were in the position shown in FIG. 3, the liquid would flow by gravity back along the bottom of the nasal cavity and into the pharynx but would not enter the rear of the oral cavity (18). FIGS. 2 and 4 show the head being held at a safe angle of tilt that allows the liquid to both reach the walls of the nasal cavity and to flow safely into the oral cavity of the mouth (18) rather than down toward the lungs.

FIGS. 1, 2 and 3 show a single container as a reservoir for the liquid (6,16). The container in FIGS. 1 and 2 is an open cup embodiment made by trimming a cup having a cylindrical wall (8) a bottom (7) and a rim (2) trimmed to fit against the face only under (1) and along side (4) the nose and trimmed to be lower (3) in the front (8) and the back trimmed to allow a seal against a person's face only when the angle of the device with the top of the face is at its angle of fit. Both embodiments in the drawings are shown to have an angle of fit that is less than ninety degrees illustrating that the head must be tilted forward at an angle greater than generally upright to allow a liquid tight below the nose seal (1,12) and cheek seals (4,13), illustrating the pooling means of communication. The device is held in the person's hand and the wall is flexible to allow shaping with the thumb (5) and fingers. While the head is tilted forward, the entire nasal cavity may be filled (9) into the pharynx (10) with liquid and excess liquid will empty into the rear opening of the oral cavity (11,18) acting naturally as a sink or drain by force of gravity.

FIG. 1 depicts an open cup embodiment prior to use, a single container as a reservoir (6) containing liquid. FIGS. 2 and 4 depict a pooling means for communicating liquid into the person's nasal cavity by submerging the person's nostrils in the pool formed to a maximum depth of the cheek seal submerging the nostrils while the head is safely tilted forward with liquid in the reservoir flowing into the pool. Either embodiment facilitates inhalation for infusing the nasal cavities of the person with liquid by simply inhaling the liquid from the pool.

FIGS. 3 and 4. depict an irregularly shaped container (16) as a reservoir for the liquid with an outlet (19) communicating in FIG. 3 the interior of the reservoir with the atmosphere and in FIG. 4 with an additional container augmenting the reservoir (20) in the form of a syringe (21), and the rim is fitted over the nose (14). If the rim fitted over the nose forms an airtight seal with the face (14) continuously with the cheek seals (13) and under the nose (12), liquid in the additional container may be either drawn into the pool of liquid submerging the nostrils and into the nasal cavity by inhalation or forced into the pool and into the nostrils by increasing the pressure in the additional container, as would occur by pressing against the top of the plunger of the syringe in FIG. 4. Inhalation and external pressure are each used for infusing the nasal cavities with the liquid, with use of the syringe (21) plunger as an external pressure source for infusing the nasal cavity of the person with the liquid. It may be seen that with the head tilted forward, liquid fills the nasal cavity beyond the end of the septum (17) to enter the mouth (18).

FIG. 3(15) depicts an activated shutting off means for restricting flow into the nasal cavity when the head is not safely tilted forward while the device is properly fitted to the face and FIG. 4 depicts the inactive shutting off means allowing communication and flow into the nasal cavities while the head is tilted forward. The shutting off means is any gravity actuated shutting off means comprising the flap (15) as a valve that shuts when the device is at a particular prescribed orientation, or equivalent means such as a ball as a valve or a mercury switch that shuts off flow to shut off the supply of liquid in communication with the nasal cavity, the reservoir or the pool.

FIG. 2 depicts a spilling means for assuring the head of the person is tilted forward. The rim is trimmed in the back to fit against the face so that the cheek seal (4) can only exist while the device is in contact with the face at its angle of fit. A shallow cheek seal as a spilling means for assuring that the head is tilted by restricting flow into the nasal cavity, the shallowness causing the pool to overflow and the content of the reservoir to dump out over the top of the cheek seal when the head is positioned generally upright while maintaining the device in proper contact with the face or through the cheek seal when contact is broken by being at an angle other than the angle of fit. The closed embodiment may comprise a spilling means for assuring proper head tilt if no liquid or air tight seal is formed over the nose (14) continuously with the cheek seal.

Anatomically, the cavities immediately above the palate of the head naturally contain three openings, the two nostrils at the front and the third at the back just above the rear opening of the oral cavity, such that if the head is held generally upright, each are at approximately the same horizontal level. While it is possible to close the back opening through muscular action, doing so naturally prevents sucking a flow of liquid through the nostrils by inhalation or forcing a flow of a liquid which requires replacement of the air with liquid. It is well known to anyone who swims underwater that closing the back opening prevents liquid from entering through the nostrils by preventing replacement of the trapped air.

Whereas, if the person is laying in the face down position, any liquids draining over the soft palate past the rear entrance of the oral cavity must drain down into the rear of the oral cavity, if the oral cavity and its rear opening are allowed to be open, by force of gravity. Any position of the head between a vertical or generally upright head and the face down position, herein referred to as a safe angle of forward tilt or safely tilted forward head position, imparts the same effect as the face down position by effectively placing the entrance into the back of the oral cavity on the floor of the windpipe and functions as a drain into the oral cavity.

This invention exploits the benefits of positioning the head and neck in a forward tilted position greater than a generally upright position and infusing the nasal cavity through both nostrils, a combination which has not been described in the prior art.

If the liquid is allowed into the nasal cavities of the head and the head is kept in a generally upright position the liquid naturally flows along the bottom or floor of the nasal cavity over the soft palate straight down the pharynx by force of gravity to either be swallowed, to be passed into the lungs or to be expelled by uncontrolled reflexive coughing as it enters into the lower regions of the pharynx and windpipe. This is a survival mechanism to prevent liquids reaching the trachea, bronchia or the lungs.

FIG. 4 illustrates that if the head is safely tilted forward, the nostrils tend to effectively become the bottom of the nasal cavities and the back opening effectively becomes higher and thus tends toward being the effective top of the container formed by the nasal cavity. It should be noticed that if the head is tilted at any angle greater than approximately forty-five degrees for the average person, though the angle may vary, the back opening effectively becomes the absolute top of the container formed by the nasal cavity. With this observation, it may be seen that between a forward tilt which is almost upright but greater than generally upright to an angle which is almost forty-five degrees, a variable degree of the front and lower regions of the nasal cavity will be in contact with the liquid contained therein.

Further, if liquid does escape through the back of the nasal cavity and down toward the windpipe, with the head safely tilted forward, anatomically the opening into the mouth is effectively found along the floor of the windpipe and the liquid drains into the mouth rather than continuing further along the windpipe.

This invention is intended to take advantage of the foregoing facts. If one attempts to flood the nasal cavities of the head by inhalation but fails to tilt the head at a safe forward angle of tilt, one possible result is that the recipient of the liquid will drown or suffer induced uncontrollable coughing and choking, and if the intended purpose is to infuse the nasal cavities with the liquid, the attempt would fail since the liquid would simply flow along the floor of the nasal cavities along the hard palate, and out the back opening without infusing the upper regions of the cavities, which is illustrated in FIG. 3.

Shown in FIG. 2, a cup (8) having a diameter smaller than the size of a user's head is most convenient and is preferred, and substantially smaller is most preferred, so the cup wall is cut at an angle along a diagonal plane to form the rim to allow for both the cup to be tilted back which is necessary to cause the liquid to flow toward the face and the head to be safely tilted forward which is necessary to satisfy the method of the invention using inhalation.

In FIG. 1 the rim at the front (3), shows the lowest point of the cup wall defining a measurable amount of liquid to be used, though graduations for lesser amounts may be provided. FIG. 1 shows the cutout in the cup wall (1) that forms a fit along the upper lip and the cheek to form the cheek seal. If the diameter of the cup is small, the cutout (4) and the curvature of the wall shown in FIG. 1 effectively forms a trough while the cup is tilted backward having two trough walls and a floor. The trough walls along with the cheek seal prevent the liquid from spilling out laterally during use while allowing enough depth of liquid to submerge the nostrils and if shallow enough to just submerge the nostrils when the head is at a predetermined safe angle of tilt, the shallow side walls are a part of spilling means for assuring the head is at least tilted at the predetermined angle for open embodiments.

If the cup has a large diameter or the shape of the nostrils or the shape or size of the nose should tend to prevent the nostrils from being submerged during use, the side walls of the trough are flexible to allow the thumb (5) and forefingers to squeeze the cup effectively slightly increasing the arc or u-shape, that is, decreasing the radius of the arc or u-shape, of the line of the seal under the nose above the upper lip, increasing the height of the cheek seal. The upper portion of the arc or u-shape tend toward the cheeks of the user alongside the nose (4) forming the cheek seal shown in FIG. 2 showing a short cheek seal as a part of the spilling means for assuring the head is safely tilted as a safety feature while the cheek seal is maintained and the depth of the effective trough formed by the side walls of the trough should not be so deep as to allow the nostrils to be submerged while the head is generally upright or more upright than a predetermined angle without spilling the liquid depending on how the cup rim is trimmed.

The cup shown in FIG. 2 may be of any shape such as the container shown in FIGS. 3 and 4 so long as the functionality of the device is present. The liquid shown in FIG. 4 is either sucked by inhalation or forced by pressure into the nasal cavity through the nostrils. Inhalation is inhaling liquid into the nasal cavity with the mouth closed. External pressure for infusing the nasal cavity is forced reduction of volume of a closed sealed environment in communication with the nasal cavity such as depressing the plunger of a syringe (21) or squeezing a bulb, or by gravity flow as in an ordinary douche bag, or forced increases in the volume of the liquid as with use of a pump in sufficient quantity to fill the nasal cavity while maintaining an air tight communication between the container and the nasal cavity through the nostril openings. The invention would equally well comprise use of a tubing means as equivalent to the pooling means for establishing an airtight communication through the nostril openings between a container and the nasal cavity using a hollow tube or hose fitted not into one nostril opening, as described in the prior art, but one in each of the nostril openings. As with the pooling means, an embodiment comprising the tubing means may additionally comprise a shutting off means for assuring a safe forward angle of tilt of the head during use by restricting the fit of the device to be at a fixed angle of fit with the face during use as in FIGS. 3 and 4 and comprising a shutting off means for shutting off flow equivalent to the valve of FIGS. 3 and 4.

What is claimed is:

1. A method for introducing a liquid into the nasal cavity of a person through both nostril openings essentially while the head of the person is safely tilted forward at an angle greater than generally upright comprising the steps of:

establishing an airtight communication by pooling or tubing means between an external source of the liquid and the nasal cavity of the person through both the nostril openings;

filling or partially filling the nasal cavity with the liquid by inhalation or external pressure means for infusing the nasal cavity while the head of the person is safely tilted forward; and diverting any excess liquid reaching the pharynx away from the lungs by allowing any of the excess liquid to pass into the rear of the oral cavity and into the mouth while the head of the person is safely tilted forward.

2. A device for filling or partially filling the nasal cavity of a person with a liquid through both nostril openings of the person while the head of the person is safely tilted forward comprising:

a container or communicating containers of the liquid;

means for establishing communication between the liquid and the nasal cavity of the person through both nostril openings of the person while the head of the person is safely tilted forward greater than generally upright; and means for filling or partially filling the nasal cavity of the person with the liquid by either inhalation or external pressure.

3. The device of claim 2 further comprising means for assuring that the head of the person is at a safe forward angle of tilt during use.

* * * * *